(12) United States Patent
Wang

(10) Patent No.: US 6,628,815 B2
(45) Date of Patent: *Sep. 30, 2003

(54) COMPUTER-AIDED DIAGNOSIS SYSTEM AND METHOD

(76) Inventor: Shih-Ping Wang, 409 Becker La., Los Altos, CA (US) 94022

( * ) Notice: Subject to any disclaimer, the term of this patent is extended or adjusted under 35 U.S.C. 154(b) by 0 days.

This patent is subject to a terminal disclaimer.

(21) Appl. No.: 10/010,554

(22) Filed: Nov. 2, 2001

(65) Prior Publication Data
US 2002/0054697 A1 May 9, 2002

Related U.S. Application Data

(60) Division of application No. 09/798,756, filed on Mar. 2, 2001, now Pat. No. 6,434,262, which is a continuation-in-part of application No. 08/890,254, filed on Nov. 28, 1997, now abandoned, which is a continuation-in-part of application No. 08/579,802, filed on Dec. 28, 1995, now Pat. No. 5,828,774, and a continuation-in-part of application No. 08/438,432, filed on May 10, 1995, now Pat. No. 5,729,620, which is a continuation-in-part of application No. 08/129,255, filed on Sep. 29, 1993, now abandoned.

(51) Int. Cl.[7] ................................................. G06K 9/00
(52) U.S. Cl. ........................................... 382/132; 378/4
(58) Field of Search ................................. 382/132, 128, 382/274, 131; 378/54, 4, 21, 37, 98.2; 600/407; 250/587

(56) References Cited

U.S. PATENT DOCUMENTS

| | | | | |
|---|---|---|---|---|
| 5,399,470 A | * | 3/1995 | Dickerson et al. | 430/139 |
| 5,440,130 A | * | 8/1995 | Cox et al. | 250/370.09 |
| 5,537,485 A | * | 7/1996 | Nishikawa et al. | 382/130 |
| 5,644,650 A | * | 7/1997 | Suzuki et al. | 382/132 |
| 5,729,620 A | | 3/1998 | Wang | |
| 5,828,774 A | | 10/1998 | Wang | |
| 6,266,435 B1 | | 7/2001 | Wang | |

OTHER PUBLICATIONS

U.S. application Ser. No. 09/891,676 filed Jun. 26, 2001
U.S. application Ser. No. 09/891,676 filed Sep. 5, 2001.

* cited by examiner

*Primary Examiner*—Bhavesh M. Mehta
*Assistant Examiner*—Barry Choobin
(74) *Attorney, Agent, or Firm*—Cooper & Dunham LLP

(57) ABSTRACT

An x-ray system acquires an initial low-contrast, wide latitude (G=2.5, or G=2 or less) x-ray image of a breast. A processing system automatically finds suspected abnormalities in the breast by processing the low contrast initial image, and then automatically converts the initial x-ray image to a high-contrast, narrow latitude image at the locations of the found abnormalities to thereby facilitate diagnosis and patient care. The technology includes effective ways to produce, process and display the various images, and can be extended to other types of images.

10 Claims, 7 Drawing Sheets

COMPUTER-AIDED DIAGNOSIS SYSTEM AND METHOD

REFERENCE TO RELATED APPLICATIONS

This application is a divisional of parent application Ser. No. 09/798,756 filed on Mar. 2, 2001 (now Pat. No. 6,434,262), which is a continuation-in-part of parent application Ser. No. 08/890,254 filed on Nov. 28, 1997 (abandoned). Ser. No. 08/890,254 in turn is a continuation-in-part of parent application Ser. No. 08/579,802 filed on Dec. 28, 1995 (now Pat. No. 5,828,774) and Ser. No. 08/438,432 filed on May 10, 1995 (now Pat. No. 5,729,620). In turn, Ser. No. 08/579,802 is a continuation, and Ser. No. 08/438,432 is a continuation-in-part, of parent application Ser. No. 08/129,255 filed on Sep. 29, 1993 (abandoned). This application hereby incorporates by reference the entire disclosure, drawings and claims of each of said parent applications as though fully set forth herein.

FIELD, BACKGROUND, AND SUMMARY OF THE DISCLOSURE

This patent specification relates to displaying radiological images and other information in a manner believed to assist users such as physicians in reading such images and other information. More specifically, it relates to a computer-aided diagnosis "CAD") system and method for detection and identification of abnormalities in radiological images, and to using the results to produce images that provide more useful diagnostic information and better patient care. The images can be viewed in conventional format but in conjunction with viewing an annotated road map of the location and/or the identification of suspected abnormalities found through computer processing of radiological images. The annotated map highlights and/or identifies suspected abnormalities to help the image reader better assess the presence and/or meaning and significance of abnormalities in the radiological image.

The utility of the system and method is further improved by initially acquiring an x-ray image that is low-contrast but wide-latitude (G=2.5, or G=2 or less). In the case of breast imaging, a low-contrast, wide latitude x-ray image makes it possible to include in the image significant information about both very dense and much less dense tissue whereas normal x-ray film (typically G=3) may not record sufficient information about dense breast tissue. On the other hand, a low-contrast image may not be as suitable for viewing, and laws and regulations may prohibit the use of film of G less than 3 for breast diagnosis. In a preferred embodiment, the low-contrast image is automatically processed in the electronic domain to find suspected abnormalities, taking advantage of the fact that the wide latitude may allows the film to contain more information than conventional images. Resulting information regarding such abnormalities is in turn used as a guide in automatically converting the initial, low contrast image to a display image that is high-contrast at areas of the suspected abnormalities, to thereby facilitate diagnosis and patient care.

The detection of abnormal anatomic regions in radiological images using a computer system comprising specialized software and possibly specialized hardware has been reported. For example, in the area of mammography, representative reports are: Giger et al in the May 1993 issue of RadioGraphics, pages 647–656; Giger et al in Proceedings of SPIE, Volume 1445 (1991), pages 101–103; Doi et al in U.S. Pat. No. 4,907,156; and Giger et al in U.S. Pat. No. 5,133,020. See, also, the disclosure of and in prior art cited in said parent applications. In particular, in the area of detecting spiculated or stellate lesions in mammograms using convergent line detectors as the principal abnormal feature detection algorithm, representative reports are: N. Karssemeijer in the book entitled "Digital Mammography", edited by A. G. Gale et al, published by Elsevier in 1994, pages 211–219; and Kegelmeyer et al in Volume 191 (1994) of Radiology, pages 331–337. In the area of detecting clusters of microcalcifications in mammograms using thresholding and a clustering kernel as the principal abnormal feature detection algorithm, representative report are: Nishikawa et al in Volume 20 (1993) of Medical Physics, pages 1661–1666; and Feig et al in Volume 33 (1995) of Radiological Clinics of North America, pages 1205–30. See, also, co-pending patent applications Ser. No. 08/676.660 filed on Jul. 10, 1966 entitled "Method and apparatus for fast detection of spiculated lesions in digital mammograms," and Ser. No. 08/901,541 filed on Jul. 28, 1997 entitled "Method and system for using local attenuation in the detection of abnormalities in digitized medical images." These two patent applications and each of the other references cited in this patent specification are incorporated herein by reference as though fully set forth herein. These systems are generally referred to as Computer-Aided Diagnosis ("CAD") systems, and are believed to be particularly useful to radiologists in the diagnostic process and particularly in screening radiological procedures. R2 Technology, Inc. of Los Altos, Calif. offers technology under the trade name ImageChecker and a system under the trade name ImageChecker M1000 to assist physicians in their review of screening mammograms by identifying image areas that might require further review. Information on this technology is available at www.r2tech.com.

In a screening radiological procedure, such as screening mammography, the patients typically are asymptomatic and true abnormalities (e.g. cancers) are said to occur at a typical rate of about one case per one hundred patient examinations. Reading of the mammograms, when most of them are negative, can be a tedious task that can make it difficult to maintain a constantly high attention level. Some detectable abnormalities can be missed or misdiagnosed, which can result in delayed or more costly treatment, and can even result in a reduction of patient's longevity or chance of survival. According to an article in the May 26, 1993 issue of JAMA, pages 2616–2617, the misdiagnosis rate in mammograms can be in the range of 15 to 63%. The CAD system, serving as an electronic reminder or second reader, as a spell-checker can be in a word processor, can assist radiologists in attaining higher detection rate (higher sensitivity) for abnormalities or reducing the misdiagnosis rate (lowering the false-negative rate).

Applicant understands that a current procedure using a CAD mammographic system proceeds as follows. The physician views a radiological image, reaches a preliminary diagnostic decision, and then views a separate second image displayed on a CAD system. This second image is marked or annotated with a localized identification of the abnormalities that the CAD system has detected through computer analysis of a digitized version of the conventionally obtained radiological image. After a reexamination the area of the radiological image that corresponds to the position of the detected abnormalities displayed on the CAD system, the physician makes the final diagnostic decision. This final diagnostic decision may or may not be the same as the preliminary decision, depending on whether the physician found the additional diagnostic information provided by the CAD system to be significant and, if so, what significance the physician ascribed to it. Following the final diagnostic decision, and perhaps depending on the degree of suspicion for malignancy, the physician can recommend a course of further action, which can include no further action or further follow-up examinations or biopsy.

In the process of detecting abnormal anatomic features in radiological images using a CAD system as described in the above cited references, the radiological film image of a patient is processed through a film digitizer to generate a digitized image which is input as such into the system. The digitized image is then analyzed by a digital image processing computer with specialized software and perhaps also specialized hardware for abnormal anatomic feature detection. If abnormalities are detected, an annotated radiological image is displayed on a special TV monitor, with markers placed around or adjacent the detected abnormalities. This TV monitor typically has a large dimension (typically a screen diagonal of 12 inches or larger) and a high spatial resolution (typically more than 1000×1000 pixels). Because of the large dimension and high spatial resolution, this TV monitor typically is positioned at some distance away from the film. Typically the center of the monitor is more than 12 inches from the center of the film on the conventional film illumination box. In addition, this special TV monitor typically has a low brightness and a high cost.

It is believed that the display method using a high-resolution TV monitor has certain shortcomings that make the process inconvenient and inefficient. The high-resolution TV monitor is expensive, its spatial resolution although high for monitors is still less than that of the original x-ray film, and its brightness and dynamic range are also inferior to those of an x-ray film viewed on a light box. Therefore, it is believed that a physician might not wish to rely solely on the image displayed on the TV monitor to make diagnosis, but typically would repeatedly go back to the conventional film illumination box to view the original film image. This can lead to the loss of valuable time and can be uncomfortable at least because of the different brightness levels and spatial resolution levels of the two images. In addition it is believed that diagnostic errors can arise from the need for the physician to shuttle back and forth between two different displayed images. Even when a potentially true abnormality (cancer) is detected and pointed out by the CAD system to the physician, the fatigue and eye discomfort and other effects due to viewing two images of such different characteristics may still cause the physician to miss the significance of the corresponding area on the original x-ray film and to fail to notice or appreciate the abnormal features of the detected abnormality and decide to ignore the detected abnormality.

Accordingly, one object of this patent specification is to provide an improved combined display of an x-ray radiological image and CAD-detected abnormalities from the x-ray image. A more specific object is to provide the CAD user with further processed, annotated and enhanced image representations of regions around the CAD detected abnormalities in order to emphasize abnormal image features of these detected abnormalities. Another more specific object is to produce an initial image that is low-contrast but wide latitude and use it to automatically find suspected abnormalities, and use information about the suspected abnormalities to automatically convert the initial image to a display image that is high-contrast at the density range of the found abnormalities. The ultimate goal is to help the user (physician) better assess the type and degree of abnormality of these detected abnormalities in the radiological image.

Another objective is to present the further processed image of the area around the CAD detected abnormalities on a display such as a small TV monitor located close to the x-ray film during viewing of the x-ray film. The term TV monitor is used generically, to refer to any type of electronic display, for example a flat panel display. The two images should be so close and should otherwise match each other such that eye and other discomfort due to viewing two different images alternately would be reduced. Still another object is to print the annotated road map and/or the further processed image representations of areas around the CAD detected abnormalities on the same sheet of photographic film that contains a printout of the radiological image.

This patent specification describes in detail, toward the end, the preferred embodiment that derives a low-contrast, wide latitude image, automatically extracts information about suspected abnormalities therefrom, and uses that information to automatically produce a display image that is high-contrast at the areas of the suspected abnormalities. Earlier parts of the patent specification describe embodiments involving primarily various ways to obtain an x-ray image, extract information regarding suspected abnormalities, and display that information in ways that facilitate diagnosis and treatment.

In an exemplary and non-limiting first embodiment, the further processed image of areas around the CAD detected abnormalities from a radiological film is presented on a small TV monitor, located in close proximity to the radiological film being viewed at the light box. The display of this further processed image shares (e.g., is toggled on) the small TV monitor with the display of a miniaturized annotated road map. On demand by the CAD user, e.g. the physician using a toggle switch, the miniaturized annotated road map image and the further processed image representations such as tiles of areas around the CAD detected abnormalities are displayed alternatively on the small TV.

In an exemplary and non-limiting second embodiment, the miniaturized annotated road map image is presented on a small TV monitor and further processed image tiles of areas around the CAD detected abnormalities are presented on a second and separate small TV monitor. Both small monitors preferably are located in close proximity to the radiological film being viewed at the light box.

In an exemplary and non-limiting third embodiment, the radiological image is acquired through digital means, and thus is in digital form initially. The radiological image can be displayed as an electronic image on a high-resolution monitor. The annotated map and, if desired the tiles as well, can be displayed on the same monitor, at an area that does not overlap with the areas of interest of the displayed radiological image. In some cases, the digitally acquired radiological image is printed on a sheet of photographic film for later viewing on a light box. In that case, the annotation road map and, if desired the tiles as well, can be printed on the same sheet of photographic film, at an area that does not obscure relevant parts of the radiological image.

In an exemplary and non-limiting fourth embodiment, a CAD system is used to enhance the informational content of image displays, by taking an initial radiographic image that has a low contrast but wide latitude. This allows imaging well on the same film or other imaging system of tissues that differ greatly in density. The initial image is processed to identify area of possible interest, such as areas of suspected abnormalities. Based on characteristics of these areas, the initial image is converted to a display image that has high contrast at the density range(s) of the already identified areas of possible interest and thus can provide enhanced diagnostic information and assist in any further treatment.

DETAILED DESCRIPTION

Figure 1:
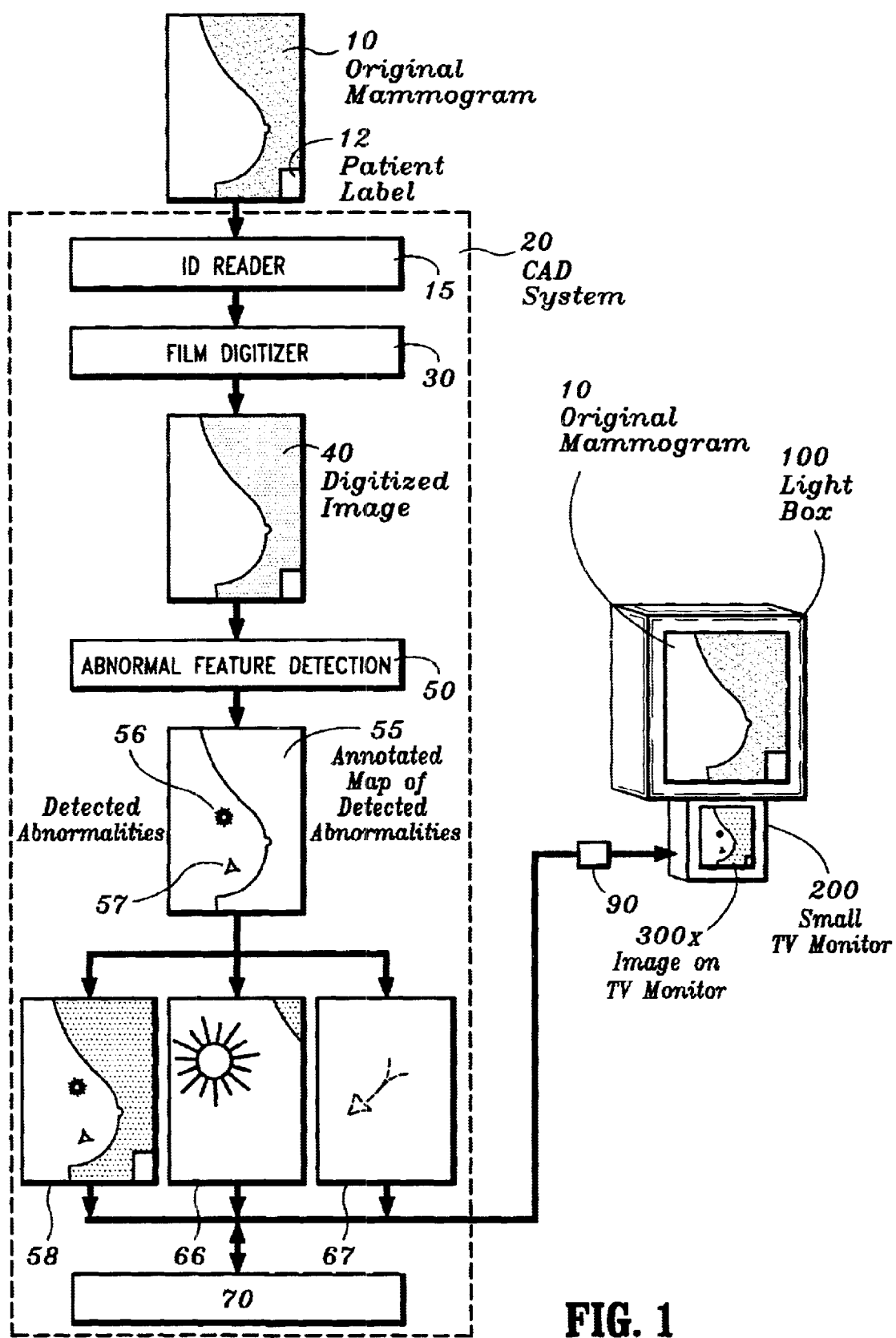
FIG. 1 is a block diagram illustrating a CAD system and its output display according to a first embodiment.

Referring to FIG. 1, a preferred but non-limiting example of a first embodiment generates an annotated road map of CAD-detected abnormalities and a further processed image of the area around the CAD detected abnormalities from a radiological film. The annotated road map and/or the further processed image are displayed on one or more small TV monitors located in close proximity to the radiological film being viewed at a light box. In this example, the radiological film is in the form of a mammographic x-ray film acquired with a conventional mammographic film-screen imaging system. The original analog two-dimensional mammographic x-ray film 10, with a patient information label 12 printed at an edge of the film, is sent through a film digitizer 30 of a CAD (computer-aided diagnosis) system 20. This system 20 can be the system disclosed in the U.S. patent applications incorporated by reference herein, and generates a digitized two-dimensional mammographic image 40. Preferably, the film digitizer 30 should be a laser film digitizer or a high performance CCD based film digitizer and should have a dynamic range and a spatial resolution comparable to those of the original mammographic film. Such film typically has a dynamic range of 10,000:1 and spatial resolution of approximately 50 microns per pixel (or about 4,000×5,000 pixels for 8-inch×10-inch film. The identity of the original mammographic image 10 is entered into the CAD system at this point to identify the digitized mammographic image 40 and thus the original film 10. An useful option at this point is to automatically input the identity of the original mammographic image 10 into the CAD machine. This can be accomplished in many ways—for example, by labeling the mammographic film 10 with a code such as a bar code close to the a patient information label 12 printed on the edge of the film, or by incorporating the bar code into the patient information label 12. The label can then be read into the CAD system 20 with an optional ID bar code reader 15 as the mammographic film 10 is being fed into the film digitizer 30.

The digitized mammographic image 40 is then sent through an abnormal feature detection stage 50 of the CAD system, or CAD machine, 20. The findings or results, positive or negative in nature, from the abnormal feature detection stage 50 typically are in the form of a two-dimensional annotation map 55. The map identifies the locations and types of the CAD-detected abnormalities 56 and 57 (in this illustrative example) present in the original film image 10. For the purposes of an illustration, let the abnormality 56 be a spiculated lesion and let its location on the annotated map be marked with a star-shaped marker. Let the abnormality 57 be a cluster of microcalcifications and let its location on the annotated map be marked with a triangular shaped marker. Thus, the markers identify not only the detected location but also the detected nature of the suspected abnormality identified at this stage. The annotation map 55 can be scaled down to a sub-sampled image, say 512×512 pixel in size and 8-bit in gray scale, as the digitized image 40. The two superimposed images, 55 and 40, in registration with each other, form a miniaturized annotated road map image 58. Enhanced image areas or tiles 66 and 67 are centered around the CAD-detected abnormalities 56 and 57, respectively, and can be, for example, 512×512 pixel in size and 8-bit in gray scale. They are generated by further image processing the regions in the digitized image 40 which correspond to the CAD detected abnormalities 56 and 57. The CAD-generated annotation map 55, the miniaturized annotated road map image 58, the enhanced image tiles 66 and 67, together with the digitized image 40 and its corresponding identification, can be stored for later use in an optional memory storage unit 70.

The annotation road map 58 and the enhanced image tiles 66 and 67 are transferred to an output display section of the system for display. The output display section of the CAD system can be a part of the total CAD system, in which case the data transfer can be through a dedicated shielded cable. Or, the output display section can be a separate system, in which case additional data storage memory can be added to the unit to store the transferred interim data, and the data transfer can be through a dedicated shielded cable or an existing network where the equipment is installed.

It is important to point out and emphasize the abnormal features of the CAD detected abnormalities to the physician. The reason is that the physician, even after seeing the location of the CAD detected abnormalities on the miniature road map 58, may still fail to notice or appreciate corresponding abnormal features on the original the x-ray film. By pointing these abnormal features out, with further emphasis, to the physician, it is believed that the physician would be in better position to assess the level and nature of abnormality of these CAD detected abnormalities. The principal abnormal feature detection algorithms used in the abnormal feature detection stage 50 to detect the abnormalities can be used to further emphasize the abnormal features of the CAD detected abnormalities. For example, in the case of the abnormality 56, the principal abnormal feature used to detect the spiculated lesion can be a set of convergent lines. Since the presence of the convergent lines around a lesion raises the probability of malignancy, it is believed that there would be less a chance that the physician could ignore the lesion if the convergent lines were made more noticeable. Therefore, this set of convergent lines around the spiculated lesion could be contrast and edge enhanced to form the image tile 66. For example, FIG. 3(B) of Karssemeijer article cited shows a set of detected pixels pointing to the center of a suspected spiculated lesion. Superimposing these detected pixels on the image can form the image tile 66. In the case of the abnormality 57, the principal abnormal feature used to detect the cluster of microcalcifications can be the small clustering of three or more high contrast spots. This small clustering of high contrast spots can be enhanced in brightness to form the image tile 67. The formation of this small clustering of bright spots can be of great interest to the physician. This is because the probability of malignancy is higher for a linear or branching formation. Therefore, this small clustering of high contrast spots can also be magnified in size, for example by a factor of 2 or more, to form the image tile 67 in order to help the physician see the formation of these bright spots clearly in the image tile 67. In this manner, it is believed that the CAD user, the physician, after seeing the enhanced abnormal image features of these detected abnormalities and reexamining the original x-ray image, can better assess the level of abnormality of these detected abnormalities in the x-ray image.

Also shown in FIG. 1 is an illustration of a CAD output display consisting of a conventional film illuminator, commonly called a light box, 100 and a small TV monitor 200 according to the first embodiment. In this exemplary embodiment, the miniaturized annotated road map 58 and the enhanced image tiles 66 and 67 are alternatively or sequentially displayed as images 300$x$, by operating a toggle switch 90 to display one image at a time (where x=a, b and c) on the small TV monitor 200 located in close proximity to the original film 10. Respectively, the image 300$a$ represents the miniaturized annotated road map 58, the image 300$b$ represents the enhanced image tile 66 around the CAD detected spiculated lesion, and the image 300$c$ represents the enhanced image tile 67 around the CAD detected cluster of microcalcifications. If more abnormalities were detected, there would be images 300$d$, 300$e$, etc. to be toggled through the small TV monitor.

The dimensions of the display screen of the small TV monitor 200 in this example preferably, but not necessarily, are of the order of ¼ to ½ of the dimensions of original film 10. In addition, the small TV monitor 200 should preferably be located as close as practical to the light box 100 displaying the original film 10. Preferably the center of the small TV monitor 200 should be less than 12 inches from the center of the original film 10 on the conventional film illumination light box 100. The preferred position, as shown in FIG. 1, for mounting the small TV monitor 200 is just beneath the light box 100 that displays the original image 10. It is also convenient to display a pair of images on each TV monitor, since frequently a pair of the original mammographic films 10, such as the mammograms of the left and right breasts, are displayed and viewed next to each other. In this manner, the physician still has to minimally move his or her eyes back and forth between the original radiological film image 10 on the film illuminator 100 and the images 300$x$ displayed on the small TV monitor 200. The spatial resolution of the small TV monitor 200 can be in the range of 500 TV lines, or comparable to that of NTSC or PAL. The brightness level of the small TV monitor 200 should be similar to that of the average brightness transmitted through the original film 10, so that the observer would not be bothered by a change in brightness. In using the CAD system as a second reader in a screening situation, it is sometimes preferred that the display on the small TV monitor 200 can be easily toggled with on-off with a switch 90 by the observer. As a variation, more than one monitor 200 can be used; for example, one can display the annotated map 58 and at least one other monitor can display one or more of the tiles. The tiles can be displayed on a single monitor, by toggling from one to another, or each of two or more tiles can be displayed at a respective monitor. The one or more monitors can be placed at positions relative to the light box other than those illustrated in FIG. 1

Figure 2:
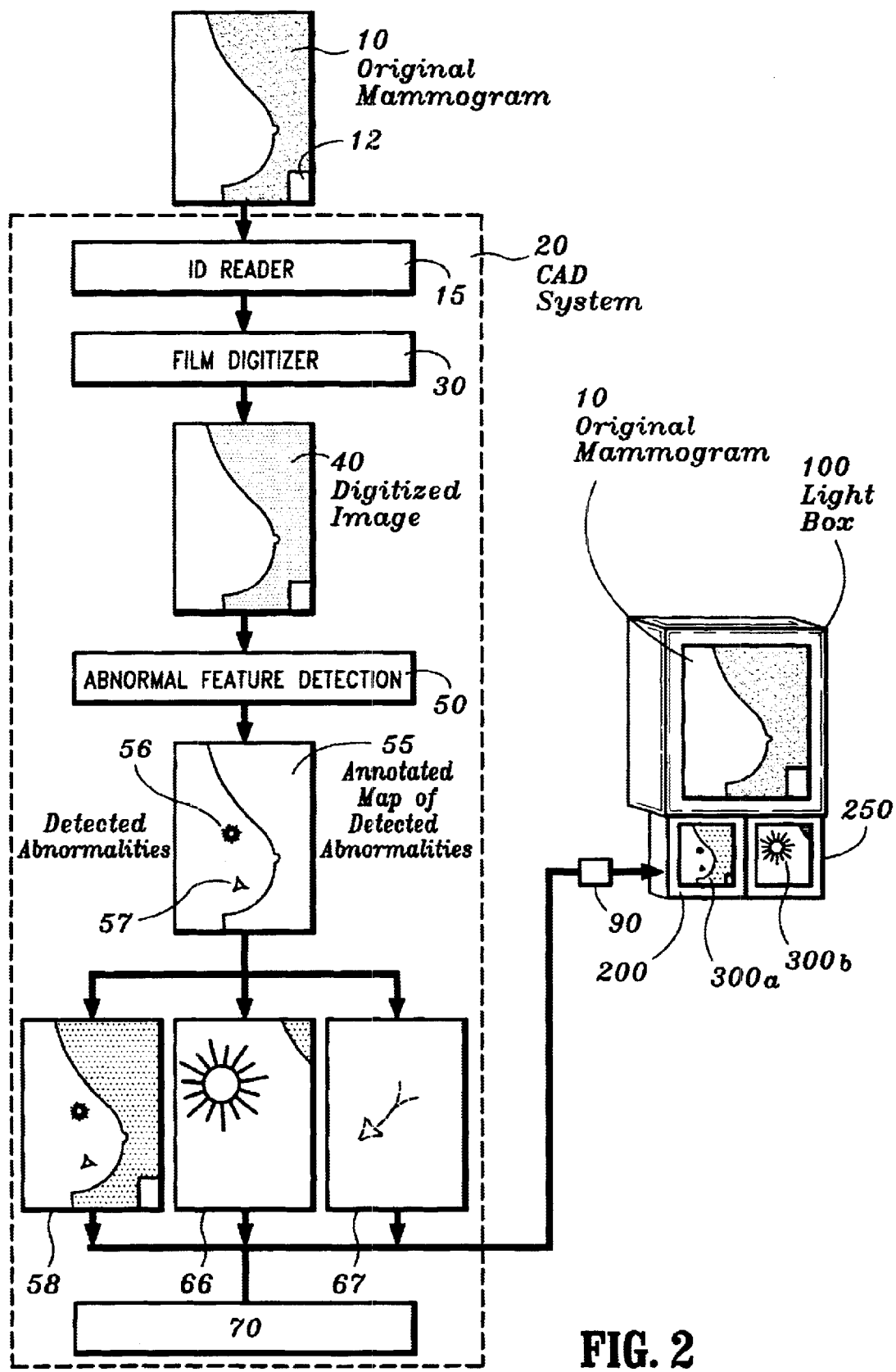
FIG. 2 is a block diagram illustrating a CAD system and its output display according to a second embodiment.

FIG. 2 is similar to FIG. 1 in many respects, and similarly labeled components serve a similar function and therefore will not be described again in detail. FIG. 2 shows a CAD output display comprising a conventional film illuminator 100 and, in this case, two small TV monitors 200 and 250, according to a second embodiment. In this exemplary embodiment, the annotated information 58 is presented as a miniaturized annotated road map image 300$a$ on the first small TV monitor 200, located in close proximity to the original film 10. The enhanced image tiles 66 and 67 are alternatively or sequentially presented, by operating a toggle switch 90, as images 300$b$ and 300$c$ on the second small TV monitor 250, located next to the first small TV monitor 200 and in close proximity to the original film 10. It is sometimes preferred that two or more small TV monitors are used, in place of monitor 250, to display the further processed image tiles 66 and 67 such that each detected abnormality is displayed on a separate small TV monitor at the same time. The small TV monitors 200 and 250 can be placed at other positions relative to the light box 100, e.g. to the side or above light box 100. More than one monitor can be used to display the tiles.

Figure 3:
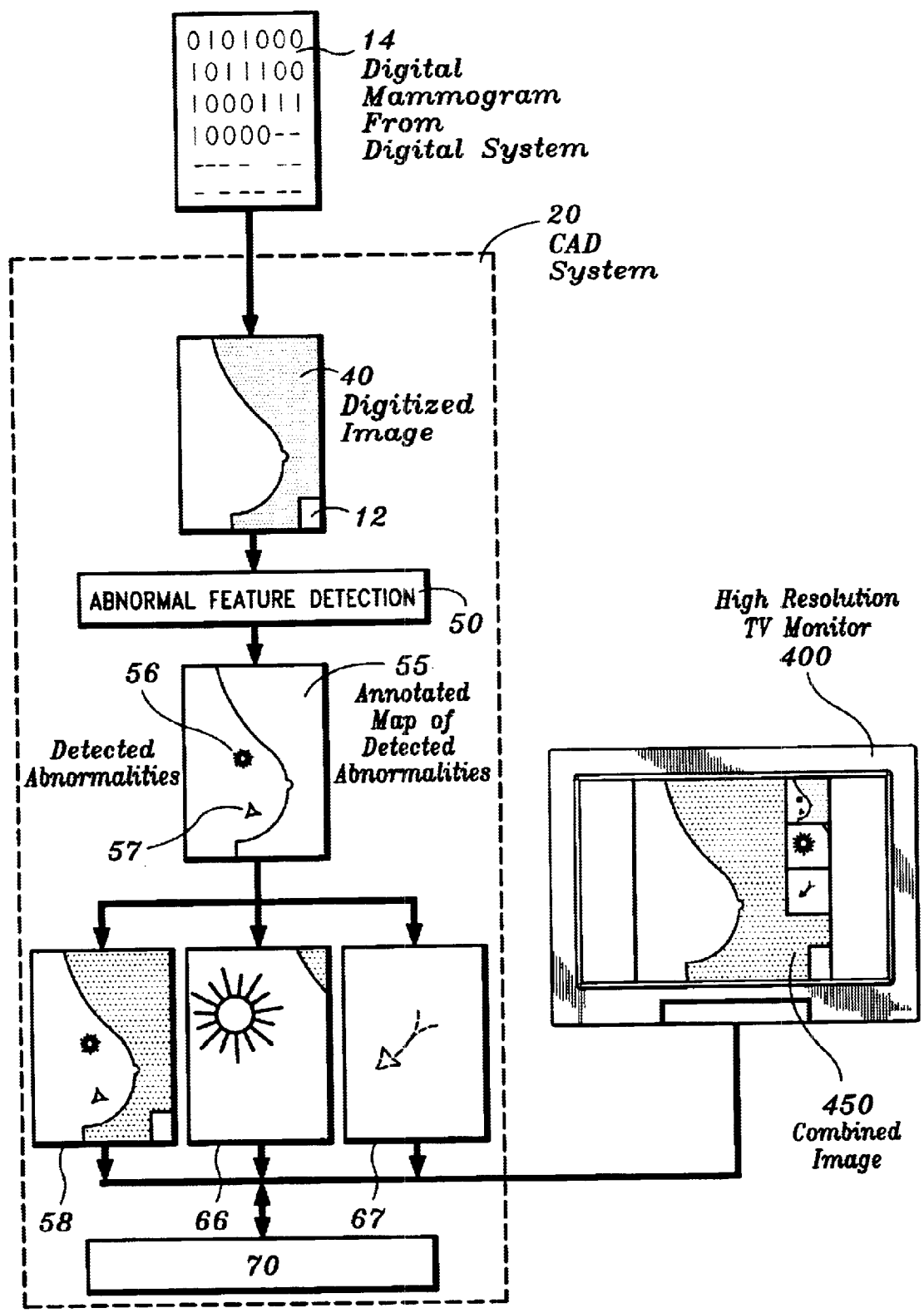
FIG. 3 is a block diagram illustrating a CAD system and a first method of output display according to the third embodiment.

Referring to FIG. 3, a preferred but non-limiting example according to a third embodiment receives radiological images which already are in the digital format detects abnormalities on these radiological images with a CAD system, and prints out the radiological images together with CAD results on photographic film. Again, components labeled the same as in FIGS. 1 and 2 serve similar functions and therefore will not be described again in detail. Digital imaging systems that provide images in digital form include but are not limited to magnetic resonance imaging ("MRI") systems, computed tomography ("CT") systems, ultrasound imaging systems, scintillation cameras, computed radiography ("CR") systems (such as Fuji's CR system based on stimulated emission phosphor detector), and recently reported and introduced digital radiography and digital mammography systems (for example, see Feig article cited earlier; using CCDs or amorphous silicon array detectors), and recently popular digital mammography and other x-ray systems using flat panel x-ray detectors. In this example, the radiological image is in the form of a digital mammogram, which is acquired with a digital mammography system. This digital mammogram 14, already having properly encoded identification and patient information 12, is reformatted into the digitized mammographic image 40 and is sent through the abnormal feature detection stage 50 of the CAD machine 20. If the information is already properly formatted for the CAD machine 20, it is sent directly to and through the abnormal feature detection stage 50 of the CAD machine 20 without reformatting. The initial film digitization step used in the first and second embodiments for analog mammograms is not needed in this case. As in the first and second embodiments, the findings or results, positive or negative in nature, from the abnormal feature detection stage 50 are in the form of a two-dimensional annotation map 55 showing the locations and types of the CAD-detected abnormalities 56 and 57. For the purposes of an illustration, let the abnormality 56 be a spiculated lesion and let its location on the annotated map be marked by a star shaped marker. Let the abnormality 57 be a cluster of microcalcifications and let its location on the annotated map be marked by a triangular shaped marker. The annotation map 55 can be scaled down to the same size of a sub-sampled image, say 512×512 pixel in size and 8-bit in gray scale, of the digitized image 40, and the two superimposed images in registration with each other form a miniaturized annotated road map image 58. Enhanced image tiles 66 and 67, centered respectively around the CAD-detected abnormalities 56 and 57, say 512×512 pixel in size and 8-bit in gray scale, are generated by further image processing the regions in the digitized image 40 which correspond to the CAD detected abnormalities 56 and 57. The CAD-generated annotation map 55, the miniaturized annotated road map image 58, the enhanced image tiles 66 and 67, and together with the digitized image 40 and its corresponding identification, can be stored for later use in an optional memory storage unit 70.

The annotation road map 58 and the enhanced image tiles 66 and 67 are transferred to the output display section of the system for display. There are several methods to display the CAD results and the digitally acquired mammogram. Since the digital system produces no film to start with at the acquisition, the first method is a totally filmless display by using a high resolution TV monitor 400. The resolution should be at least 1000×1000 pixels. In this method the annotation road map 58, the enhanced image tiles 66 and 67, and the digital mammogram 40 are all displayed on the same TV monitor as a combined digital image 450 as shown in FIG. 3. The annotation road map 58 and the enhanced image tiles 66 and 67 are shown placed at the edge or margin of the combined digital image 450. Patient information 12 can also be displayed at the same edge or margin of the combined digital image 450. The annotation road map 58 may alternatively be displayed by overlaying it on top of the digital mammogram 40. This overlay may be toggled (switch not shown) on and off so that the digital mammogram 40 can be examined without obstruction. The enhanced image tiles 66 and 67 can also be toggled (switch not shown) on and off. Alternatively, the map and tiles can be displayed on one or more monitors as in the previously disclosed embodiments.

Figure 4:
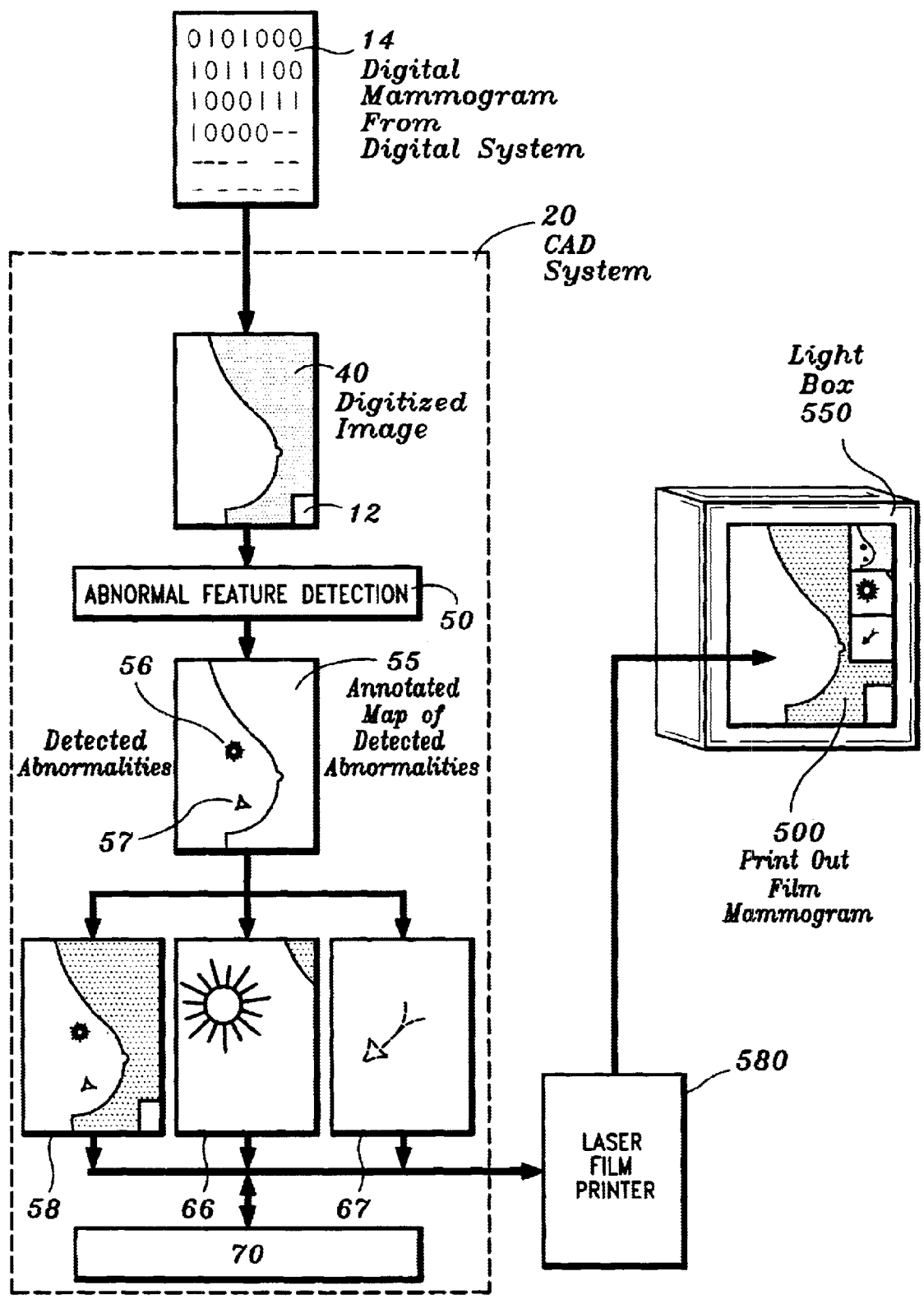
FIG. 4 is a block diagram illustrating a CAD system and a second method of output display according to the third embodiment

The second method of display, shown in FIG. 4, where the same reference numerals have the same significance as in the earlier Figures, makes a photographic film printout of the digital mammogram 40, the miniaturized annotation road map 58 and the enhanced image tiles 66 and 67 all on a same sheet of film 500. The printout film 500 is viewed on a light box 550. Since, at the present time, physicians usually are more accustomed to a photographic film, which typically conveys information with higher spatial and contrast resolution and gray scale range than a high resolution TV monitor, the second method of display can be preferred over the first method. The annotation road map 58 and the enhanced image tiles 66 and 67 are shown in FIG. 4 placed at the same edge or margin of the printout film as the patient information label 12. The photographic film printout, typically having a resolution of 4000×5000 pixels, can be made with a high resolution laser film printer 580. Such high resolution, 4000×5000 pixels, laser film printers are commercially available with a resolution of 40 microns per pixel for 8 inch×10 inch size films and 100 microns per pixel for 14 inch×17 inch size films. It is sometimes preferred that only the miniaturized annotation road map 58 be printed at the edge of the printout film 500. Alternatively, monitors can be used to display the annotated map and the tiles as in the preceding embodiments.

Digital radiological images, such as, without limitation, in the case of images from magnetic resonance imaging ("MRI"), computed tomography ("CT"), digital fluorography ("DF"), and computed radiography ("CR"), are sometimes printed out on sheets of 4000×5000 pixels photographic film for later viewing on a light box. Since MRI images are typically formatted into 256×256 pixels, CT images into 512×512 pixels, DF images into 1024×1024 pixels, and CR images into 2048×2048 pixels, many images from MRI or CT or CR modalities can be printed as small tiles in an array on one sheet of 4000×5000 pixels photographic film. Therefore, the CAD findings from these images can be printed as one or several of the tiles. A further refinement on the use of CAD is to reduce the number of images to be presented to the physician, for example by not presenting radiological images on which no suspected abnormalities are found by the CAD system, or by not presenting such radiological images for a second opinion or review by another professional.

Although the embodiments discussed above have been described in terms of preferred structures involving a single sheet of film, it should be apparent to those skilled in the art that this patent disclosure applies to viewing of multiple films on a multiple-film viewing station or an alternator (a multiple film viewer having pre-loaded films and a transport belt), to allow several x-ray films 10 or printout films 500 to be viewed at the same time or different times, with or without their respective annotation maps 58 and the enhanced image tiles 66 and 67.

Figure 5:
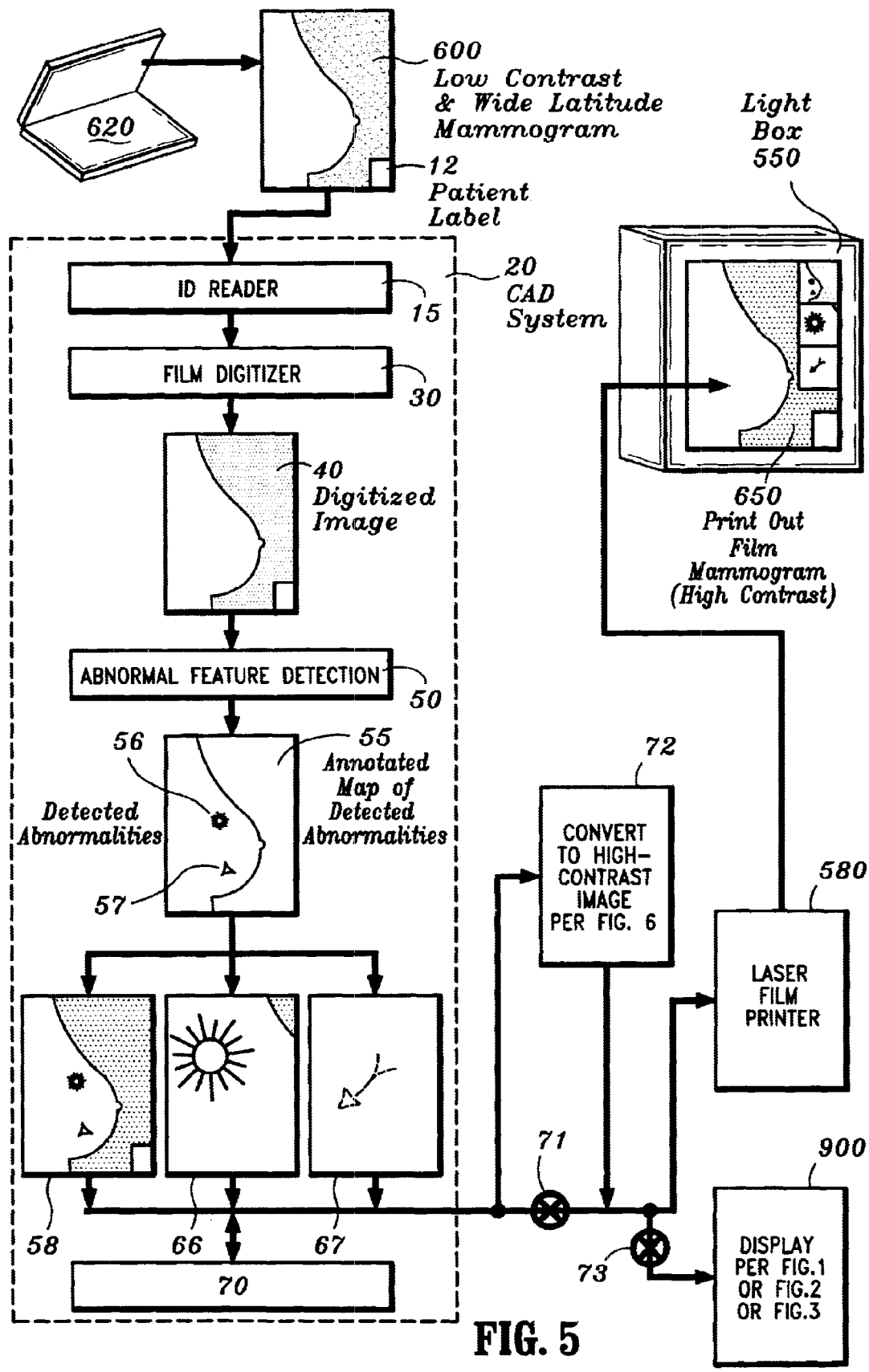
FIG. 5 is a block diagram illustrating a CAD system and an output display according to a fourth embodiment.

FIG. 5 illustrates a system in accordance with a fourth embodiment. In this example, an initial radiographic image is a low-contrast but high-latitude film image. Again, the same reference numerals have the same meanings as in the earlier Figures. The FIG. 5 system comprises an analog film-screen acquisition system and a CAD system similar to the first and second embodiments. However, in the fourth embodiment, the radiological image is acquired on a low-contrast but wide-latitude mammographic film 600. This embodiment and the third embodiment differ in the source of the digitized image 40. The acquisition system, in this example, uses a relatively inexpensive conventional mammographic intensifying screen cassette 620. The cost ratio between this screen cassette 620 and a typical current digital mammographic system can be several orders of magnitude, e.g., approximately 1000 times. The standard screen-film acquisition and exposure technique and the conventional mammographic x-ray system (not shown here) will be unchanged for use in this embodiment. The high voltage of the x-ray generator typically is in the range of 25 to 35 KVp (kilovolt peak) or, as discussed below, can be raised to a level in the 40 to 55 KVp range. By reducing the average contrast gradient G of the mammographic film 600 say from about 3.0 to about 2.0, or to 1.5 or even less, we pick up substantial gain in exposure latitude.

Figure 7:
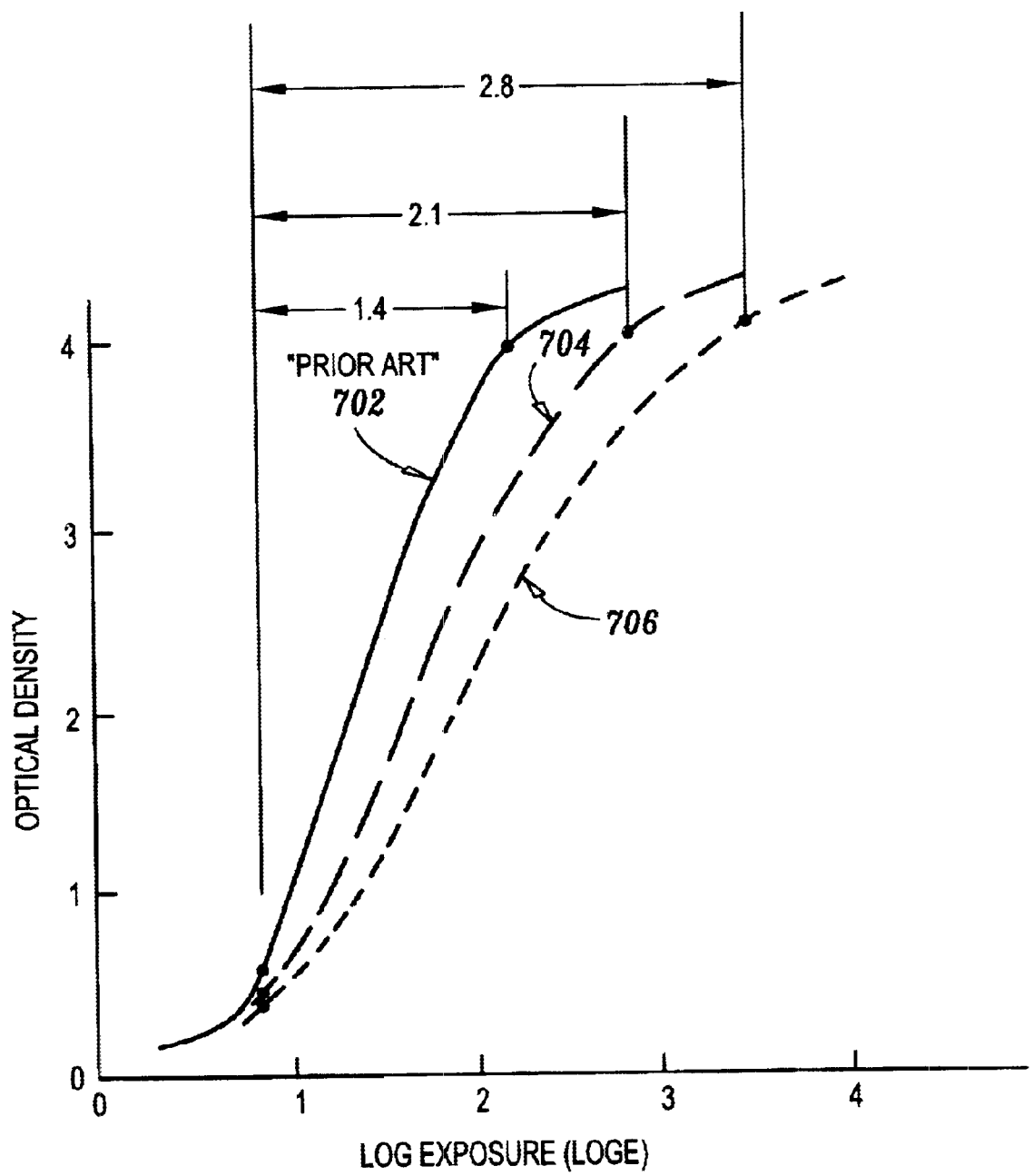
FIG. 7 compares film characteristics of wide latitude films used in the fourth embodiment with characteristics of the prior art film.

This concept of "wide latitude" is illustrated in FIG. 7, where the optical density of the film is plotted against the base 10 logarithm of the x-ray exposure (logE). The latitude is defined as the usable range of x-ray exposure, which is often expressed as the width in LogE. The conventional "prior art" mammography film is represented by the curve 702 in FIG. 7. The prior art film is shown to have a latitude of about 25 (a width of 1.4 in logE), a maximum optical density of approximately 4.2, and an average G of approximately 3.0 (maximum usable optical density divided by the width in LogE). Two examples in the range of the "wide latitude" films used in this preferred embodiment are represented by the curves 704 and 706. The 704 film has a latitude of about 125 (a width of 2.1 in logE), a maximum optical density (similar to the prior art film) of approximately 4.2, and an average G of approximately 2.0 (in this example, 4.2/2.1=2.1). The 706 film has a latitude of about 625 (a width of 2.8 in logE), a maximum optical density of 4.2, and an average G of approximately 1.5 (4.2/2.8=1.5). These are only examples, and it should be understood that this embodiment can use films of different G ratings that are substantially below 3. Preferably, the G rating of the film is 2.5 or below. More preferably, it is 2 or below. G ratings that are 1.5 and below also can be used in this embodiments.

Applicant believes that physicians may not use mammography films that have an average G rating below 3 for diagnostic viewing in mammography screening in this country. This is so because applicant understands the Congress of the United States passed a law entitled "Mammography Quality Standards Act ("MQSA") in 1992 to establish national quality standards for mammography. Mammography films with average G of less than 3 would not be able to pass the quality tests, which require the visualization of certain low contrast objects on a standard test phantom. Thus, the low-contrast but high latitude films of this embodiment are not intended for use directly for diagnostic viewing by the physician without the additional image processing described below.

The low-contrast, wide-latitude films can be produced in several ways. One way is to start with a film manufactured such that it is inherently a low-contrast, wide-latitude x-ray film and use a conventional x-ray mammograph with conventional settings to take an x-ray image. Another way is to use the same prior art film with a G rating of about 3, but to process the exposed film at a much lower temperature than conventional so that the contrast is purposely lowered to correspond to the lower G ratings discussed above. However, this approach may not be desired in at least some circumstances because the film would not be processed in the manner for which it was designed and conventional processing procedures would have to be changed. Still another way is to again use the same prior art film having a G rating of about 3, but to raise the x-ray generator high voltage substantially, say to the range of 40 to 55 KVp. The contrast of the breast is thus substantially reduced, achieving an x-ray image similar to that produced with a film having the lower G ratings discussed above. This approach has the added benefit of improved penetration of dense breast, which presently can accounts for about 40% of the screening population. The lower contrast in the breast image can be recovered by subsequent image processing because the better x-ray penetration also brings quantum statistics.

Referring again to FIG. 5, because of the low contrast (low G) effects deliberately achieved as discussed above, physicians would not be expected to make diagnosis by viewing this low contrast and wide latitude mammogram 600. The low-contrast mammographic film 600 is digitized through the film digitizer 30 and is thereby converted into a digitized image 40 that can be put through the CAD abnormal feature detection stage 50. This detection can be optimized for use with low-contrast, wide-latitude images. The result, as in earlier embodiments, is an annotated map 58 of suspected abnormalities, but in this case derived from the low-contrast image and, if desired, tiles 66 and 67. The information generated up to this point can be stored at unit 70. Depending on the setting of a switch 71, the information can be used in one of two ways. One involved displaying the low-contrast radiographic image together with the annotated map and, if desired, the tiles. To this end, the low-contrast but wide latitude image is fed through a high-resolution film printer 580 and printed out as a conventional high contrast mammogram 650. The respective annotated road maps 58 and the enhanced image tiles 66 and 67 can also be printed at the edge or margin of the mammogram 650. The physician, as in earlier embodiments, finally reads the mammogram on the light box 550. Using the miniaturized road map 58 as a guide, the physician reexamines the mammogram 650 to see if any of the CAD detected abnormalities suggest further action. The enhanced image tiles 66 and 67 provide the physician with further information by emphasizing the abnormal features of the CAD detected abnormalities. It is sometimes preferred that only the miniaturized annotation road map 58 be printed at the margin of the mammogram 650. Alternatively, depending on the setting of a switch 73, the radiological image, annotated map and tiles can be displayed at 900 in one of the ways described in connection with FIGS. 1, 2, and 3.

In order to provide an enhanced way of displaying the more relevant information, the switch 71 is set to send the low-contrast, wide latitude radiological image and information about the suspected abnormalities through a processor 72, that is explained in more detail in connection with FIG. 6. This processor, which can be a part of the same programmed computer that does some of all of the processing involved in the embodiment of FIG. 5, uses information regarding the suspected abnormalities that were automatically found by unit 50 to automatically convert the low-contrast radiological image to a high-contrast image at the density range(s) corresponding to the abnormalities. This produces a display image that can be fed to printer 580 to produce a film for display at light box 550, preferably together with a display of the annotated map alone or with the tiles. Again, depending on the setting of switch 73, the display can be additionally, or instead, on a unit 900.

Figure 6:
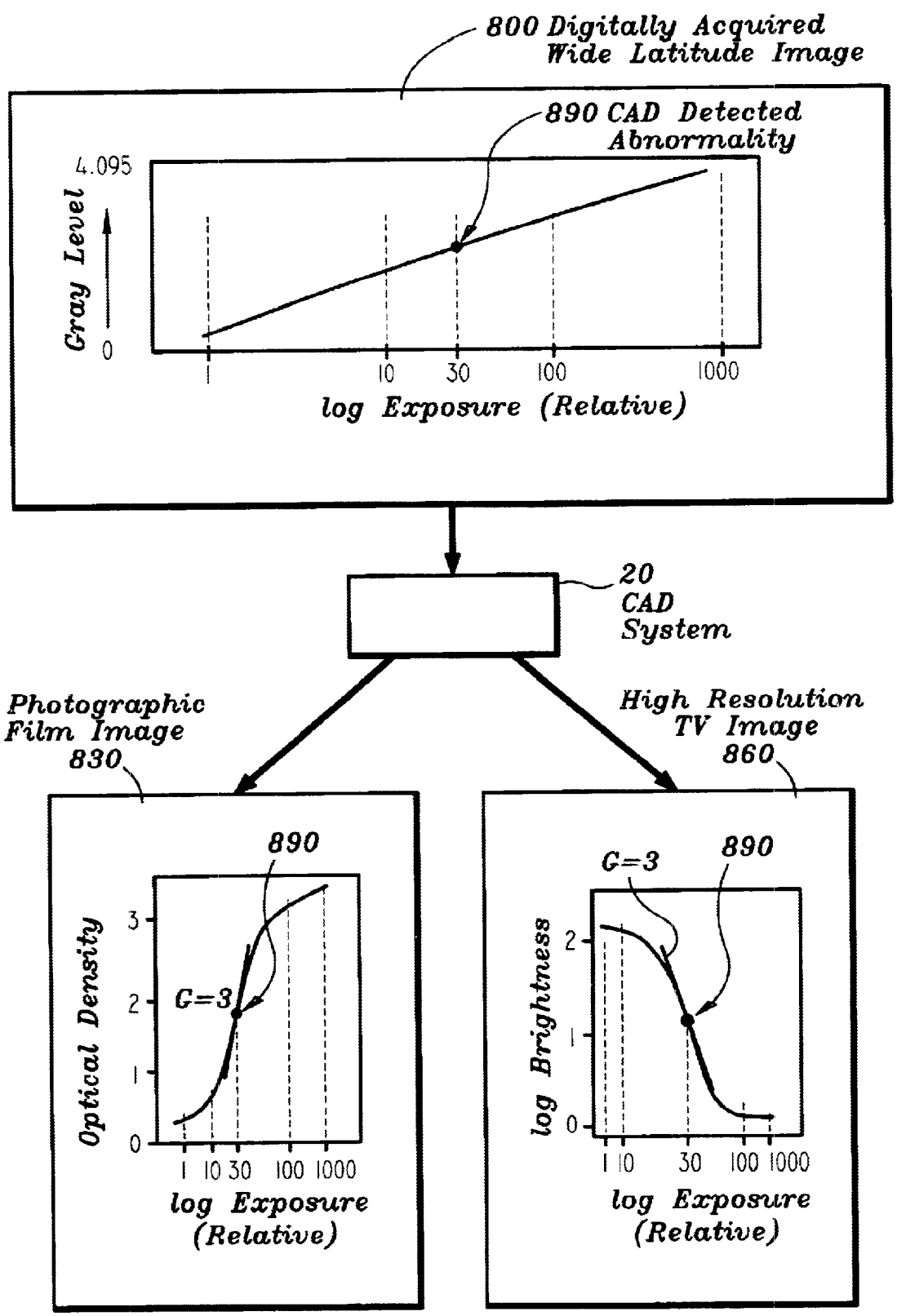
FIG. 6 illustrates displaying an output according to the fourth embodiment.

FIG. 6 illustrates how a CAD system in accordance with a fourth embodiment can be used to convert a low-contrast, wide-latitude digital radiographic image to an image that has high-contrast at areas of interest, e.g., the areas of suspected abnormalities. One of the major problems in digital imaging is how to display all the information contained in the digitally acquired images. Typically, according to Feig et al in Volume 33 (1995) of Radiological Clinics of North America, pages 1205–30, and other sources, the exposure range of the latitude (the ratio of the exposure at the highest signal region to that at the lowest signal region) of the digitally acquired image is of the order of 100 to over 1000, which is much broader than that of the display media. By comparison, if a radiogram is to be displayed on a photographic film, the exposure range of the latitude (the ratio of exposure at the highest signal region to that at the lowest signal region where the display gradient is significant) is of the order of 25 and the exposure range of the latitude of a TV monitor is less than 10.

As illustrated in FIG. 6, a CAD system 20, which can be a part of unit 72 in FIG. 5, is used guide into two different display media the display resulting from converting a low-contrast image into a high-contrast image where needed, as determined by information about abnormalities found through processing the low-contrast image. A wide latitude digitally acquired image 800 is formatted for example such that the base 10 log of its output signal (with an exposure range of over 1000) is encoded into 12 bits (4096 levels of gray). In this example, the CAD system determines how the digital, wide-latitude radiogram 800 should be printed on a photographic film 830 (having a display latitude of, for example, 25) and displayed on a high-resolution TV or computer monitor 860 (having a display latitude of, for example, 10). The radiogram 800 can be the digitized image 40 in FIG. 5. As illustrated in FIG. 6, this is done by centering the display latitude of the display medium (photographic film 830 or monitor 860) at and around the relative exposure level of the CAD detected abnormality identified at 890 on the wide latitude image 800. That is, only the range of say the relative exposure 10 to 100, around the CAD detected abnormality 890, say around relative exposure 30, is provided at the optimum contrast gradient (say G=3.0) while other image content, above or below the exposure range of the CAD detected abnormality 890, are compressed in display latitude and are displayed with reduced contrast gradient (e.g. 2.5 or less) on film 830 and/or monitor 860. The monitors would normally display the processed x-ray images; for the purposes of illustration only, FIG. 6 shows curves illustrating the relative log exposure centered around the level of interest, as determined by the fact that in this example a suspected abnormality has been detected at a relative log exposure of 30 and gray level of 890.

Although the subject matter of this patent specification has been described above in terms of preferred structures, methods and processes, it should be apparent to those skilled in the art that various alterations and modifications can be made without departing from the scope thereof and that such modifications and alterations are intended to be considered to be within the spirit and scope of the inventions defined by the appended claims.

What is claimed is:

1. A method comprising:

imaging a breast with x-rays to produce an initial image characterized by a relatively wide latitude and a relatively low contrast gradient G no greater than 2.5;

processing the initial image with a programmed computer to automatically identify suspected abnormalities in said initial image;

using information resulting from the processing step to automatically identify a latitude narrower than that of the initial image;

converting the initial image to a display image characterized by a relatively high contrast gradient G of at least 3 within said narrower latitude; and displaying the display image.

2. A method as in claim 1 in which the processing step includes generating an annotated map of said suspected abnormalities, and the displaying step comprises displaying said map as a part of or adjacent said display image.

3. A method as in claim 1 in which said imaging comprises imaging at KVp in the range of 40–55.

4. A method as in claim 1 in which said imaging comprises forming the initial image of the breast on x-ray film, and said processing step comprises digitizing the film image and processing the digitized image to identify said suspected abnormalities.

5. A method as in claim 4 in which said displaying comprises displaying the relatively high contrast image at a lightbox or alternator and displaying an image showing at least some of the suspected abnormalities near to but spaced from the displayed film image.

6. A method as in claim 1 which an image including indications of at least some of the suspected abnormalities is displayed on a TV monitor close to a display of said relatively high contrast image of the breast.

7. A method as in claim 1 in which said narrower latitude of the display image is selected to encompass density parameters of at least selected ones of said suspected abnormalities.

8. A method comprising:

imaging an anatomical structure with x-rays to produce an initial image characterized by a relatively wide latitude and a relatively low contrast gradient G no greater than 2.5;

processing the initial image with a programmed computer to automatically identify suspected abnormalities in said initial image;

using information resulting from the processing step to automatically identify a latitude narrower than that of the initial image;

converting the initial image to a display image characterized by a relatively high contrast gradient G of at least 3 within said narrower latitude; and displaying the display image.

9. A method as in claim 8 in which the processing step includes generating an annotated map of said suspected abnormalities, and the displaying step comprises displaying said map as a part of or adjacent a display of said display image.

10. A method as in claim 9 in which said imaging comprises imaging at KVp in the range of 40–55.

* * * * *